(12) United States Patent
Hansel et al.

(10) Patent No.: US 7,119,220 B2
(45) Date of Patent: Oct. 10, 2006

(54) PROCESS FOR PREPARING DIMETHYL PROPANEPHOSPHONATE

(75) Inventors: Jan-Gerd Hansel, Köln (DE); Gert Jabs, Odenthal (DE); Johannes Kaulen, Odenthal (DE); Hans-Georg Adams, Leverkusen (DE); Hans-Günter Fröhlen, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/371,290

(22) Filed: Feb. 21, 2003

(65) Prior Publication Data

US 2003/0162988 A1 Aug. 28, 2003

(30) Foreign Application Priority Data

Feb. 26, 2002 (DE) ................ 102 08 255

(51) Int. Cl.
*C07F 9/02* (2006.01)
(52) U.S. Cl. ........................... 558/137
(58) Field of Classification Search ............... 558/137
See application file for complete search history.

(56) References Cited

U.S. PATENT DOCUMENTS

| 2,478,390 A | 8/1949 | Hanford et al. ........... 260/459 |
| 3,812,222 A | 5/1974 | Kleiner et al. ........... 260/970 |
| 3,812,223 A | 5/1974 | Tsuchiya .................. 260/987 |
| 4,003,720 A | 1/1977 | Schlicht et al. ............ 44/76 |
| 4,781,865 A * | 11/1988 | Liu .......................... 562/15 |

FOREIGN PATENT DOCUMENTS

| DE | 25 35 658 | 2/1922 |
| DE | 44 18 307 | 11/1995 |

OTHER PUBLICATIONS

Houben-Weyl, Methoden der Organischen Chemie [Methods in Organic Chemistry] 4th edition vol. XII/1, Stuttgart (month unavailable) 1964, pp. 463-467, K. Sasse, "Phosphonsäuren und Derivate".
Houben-Weyl, Methoden der Organischen Chemie [Methods in Organic Chemistry], vol. E2, Stuttgart (month unavailable) 1982, pp. 351-353, Gallenkamp/Hofer/Krüger/Maurer/Pfister "Phosphosäuren und ihre Derivate".

* cited by examiner

*Primary Examiner*—Golam M. M. Shameem
*Assistant Examiner*—Ebenezer Sackey
(74) *Attorney, Agent, or Firm*—Jennifer R. Seng

(57) ABSTRACT

Process for preparing dimethyl propanephosphonate, characterized in that dimethyl phosphite is reacted with propene in the presence of a free-radical former at a reaction temperature of 60 to 95° C., the half life of the free-radical former being 0.1 to 20 min at the reaction temperature.

12 Claims, No Drawings

PROCESS FOR PREPARING DIMETHYL PROPANEPHOSPHONATE

BACKGROUND OF THE INVENTION

1. Field of the Invention

The invention relates to a process for preparing dimethyl propanephosphonate, characterized in that dimethyl phosphite is reacted with propene in the presence of a free-radical former at a reaction temperature of 60 to 95° C., the half life of the free-radical former being 0.1 to 20 min at the reaction temperature.

2. Brief Description of the Prior Art

Alkanephosphonic dialkyl esters have a broad spectrum of use; for example they serve in plastics as non-reactive flame retardants and plasticizers, and they are used as aids in textiles and paper. In addition, they are used in the chemical industry as intermediates, extraction media for metals and as additives for lubricants. Dimethyl propanephosphonate, in particular, according to DE-A-4418307 is a good flame retardant for polyurethane plastics.

A multiplicity of processes are known for preparing alkanephosphonic dialkyl esters. Because of its efficiency, free-radical addition of dialkyl phosphites to olefins is frequently used (Houben-Weyl, Methoden der Organischen Chemie [Methods in Organic Chemistry] 4th edition, volume XII/1, Stuttgart 1964, pp. 463–467; volume E2, Stuttgart 1982, pp. 351–353).

A particular technical implementation of this process is described in DE-A-2 043 520 with respect to the preparation of dimethyl propanephosphonate. The process according to DE-A-2 043 520 permits the preparation of ethanephosphonic and propanephosphonic esters in yields of greater than 95%, without telomers being formed. According to DE-A-2 043 520, the reaction of dialkyl phosphites with ethylene or propylene at 130 to 250° C. in the presence of free-radical formers must be carried out in such a manner that the gaseous olefin is added to the dialkyl phosphite present to the extent that it is reacted.

DE-A-1 963 014 describes required temperatures of 150 to 195° C. in the reaction of dialkyl phosphites with olefins. In this temperature range, all known free-radical formers should be suitable for the reaction.

A disadvantage of the above-described processes in the synthesis of dimethyl propanephosphonate is that, in the synthesis, in addition to dimethyl propanephosphonate, there is also formed 0.1 to 1.0% by weight of trimethyl phosphate which is undesirable. Trimethyl phosphate is included among the work-area substances suspected of carcinogenic activity (Deutsche Forschungsgemeinschaft, "Maximale Arbeitsplatzkonzentrationen und Biologische Arbeitsstofftoleranzwerte—Mitteilung 37" [Maximum workplace concentrations and biological agent tolerance values—Part 37], Wiley-VCH, Weinheim 2001, p. 110). In the European Union countries, preparations containing a carcinogenic substance in amounts greater than or equal to 0.1% must be appropriately labelled (directive 1999/45/EG, Annex II, Chapter 6 (previously 88/379/EWG), transposed into German law by the GefStoffV [Dangerous substances regulation]). This labelling obligation is a considerable competitive disadvantage. Trimethyl phosphate is therefore an unwanted byproduct.

Lowering the reaction, temperature does not necessarily lead to a high yield of alkanephosphonic dialkyl ester as can be implied from U.S. Pat. Nos. 2,478,390 and 4,003,720, where in the free-radical addition of dialkyl phosphites to olefins at temperatures of 60 to 150° C., telomers are predominantly formed. These telomers are unsuitable for use as flame retardant. According to U.S. Pat. No. 2,478,390, the reaction of diethyl phosphate with ethylene at 80–115° C. gives only 42% diethyl ethanephosphonate, while the remainder of the reaction product consists of high-boiling telomers.

The object underlying the invention was to provide a further improved process for preparing dimethyl propanephosphonate. As would be appreciated, the object is made more difficult by the fact that the boiling points of trimethyl phosphate and dimethyl propanephosphonate only differ by about 2° C., so that separation of the two substances by distillation can only be achieved with considerable expenditure.

SUMMARY OF THE INVENTION

In accordance with the foregoing, the invention relates to a process for preparing dimethyl propanephosphonate, characterized in that dimethyl phosphite is reacted with propene in the presence of a free-radical former at a reaction temperature of 60 to 95° C., the half life of the free-radical former being 0.1 to 20 min at the reaction temperature.

According to the inventive process it is possible, for example, to obtain a yield of greater than 95% dimethyl propanephosphonate and, in particular, at the same time, to avoid the formation of trimethyl phosphate in amounts greater than 0.1% by weight and greater amounts of telomers.

DETAILED DESCRIPTION OF THE INVENTION

The following is a more detailed description of the invention with particular reference to the preferred embodiments thereof. The temperature of the reaction according to the inventive process is preferably 70 to 95° C., very particularly preferably 80 to 95° C.

Preferred free-radical formers are those whose half life is in the range from 0.5 to 10 min at the reaction temperature. The half lives of commercially available free-radical formers are known. They may be calculated, for example, in a known manner using the Arrhenius equation from known activation parameters, or they can be determined experimentally using known methods (J. Sanchez, T. N. Myers in The Polymeric Materials Encyclopaedia, Ed. J. C. Salamone, CRC Press, Boca Raton 1996).

The free-radical former is used, preferably in substoichiometric amounts, of 0.1 to 5 mol %, in particular 0.3 to 2 mol %, based on propene. The free-radical former should be added to the reaction mixture in the same manner as the propene, so that the relative amounts of free-radical former and propene introduced remain constant over the entire period of propene addition. The free-radical former is generally added without solvent, as a solution in a solvent, or as solution in a portion of the dimethyl phosphite required for the reaction.

The free-radical formers used are preferably organic peroxides. Azo compounds and other known free-radical forming substances are also suitable.

The preferred free-radical formers include:
peroxycarboxylic acid alkyl esters (for example cumyl peroxyneodecanoate, 1,1,3,3-tetramethylbutyl peroxyneodecanoate, tert-amyl peroxyneodecanoate, tert-butyl peroxyneodecanoate, 1,1,3,3-tetramethylbutyl peroxypivalate, tert-butyl peroxyneoheptanoate, tert-amyl peroxypivalate or tert-butyl peroxypivalate), diacyl peroxides (for example diisobutyryl peroxide, di-(3, 5,5-trimethylhexanoyl) peroxide, dilauroyl peroxide or didecanoyl peroxide) and dialkyl peroxydicarbonates (for example di-(4-tert-butylcyclohexyl) peroxydicarbonate, di-(2-ethylhexyl) dicarbonate, dibutyl peroxydicarbonate, dicetyl peroxydicarbonate or dimyristyl peroxydicarbonate).

Very particular preference is given to tert-butyl peroxyneodecanoate or dilauroyl peroxide.

The molar ratio of dimethyl phosphite to propene is preferably 1.0:1.0 to 3.0:1.0, in particular 1.1:1.0 to 2.3:1.0. The dimethyl phosphite can be added without solvent, or diluted by an inert solvent. Suitable solvents are, for example, dioxane, toluene or isododecane. However, preferably it is used undiluted.

The starting substances dimethyl phosphite and propene used in the inventive process are preferably of technical grade purity. Particularly preferably, substances that are as pure as possible are used, since in this case the highest conversion rates, best yields and lowest trimethyl phosphate contents can be achieved. Very particularly preferably, dimethyl phosphite having a very low trimethyl phosphate content is used, preferably having 0 to 0.1% by weight of trimethyl phosphate, particularly preferably having 0 to 0.01% by weight of trimethyl phosphate.

The reaction according to the inventive process can be carried out, for example, under reduced or elevated pressure. Preferably, a pressure of 150 to 6 000 mbar (absolute) is employed, particularly preferably a pressure of 300 to 2 000 mbar (absolute), very particularly preferably a pressure of 500 to 950 mbar (absolute) is employed.

The reaction of the inventive process can be carried out continuously or batchwise. In the case of the continuous procedure, the reaction vessels used are preferably tubular reactors, reaction loops, reaction columns or reaction cascades. In the case of the batchwise procedure, the reaction vessels used are preferably customary reaction vessels which are known to those skilled in the art and are suitable for the said reaction conditions. These are preferably provided with external cooling. In addition, these are preferably provided with an agitating device.

To carry out the inventive process, preferably, the dimethyl phosphite is introduced and heated to the reaction temperature. The free-radical former and the propene are then added simultaneously. The period during which propene and free-radical former are added can be selected within broad ranges. It can be, for example, between 1 hour and 30 hours. However, the propene should not be added more rapidly than it is consumed by the reaction; it should be added in such a manner that the preferred pressure range is maintained.

After the end of addition, the reaction mixture can be held further at the reaction temperature to complete the reaction. It is particularly preferred to remove foreign gases before the reaction, but also, to the extent foreign gases were introduced together with the propene, during the propene addition. The removal of foreign gases can be performed, for example, by evacuating the dimethyl phosphite and/or the reaction mixture and/or by partial ejection of the gas phase in cycles or continuously. The propene can be fed onto or below the surface of the reaction mixture.

The synthesis solution can be worked up in a conventional manner by distillation which is preferably carried out at reduced pressure. If an excess of dimethyl phosphite is used, this can be recovered in the distillation and reused in the reaction.

The inventive process may be implemented advantageously in a technically simple manner, which generally results in dimethyl propanephosphonate in yields of greater than 95% and having a trimethyl phosphate content less than 0.1%. The high yields are unexpected, since the prior art processes lead to a considerable content of telomers at relatively low reaction temperatures. The low trimethyl phosphate content is a considerable technical and also economic advance, since it makes possible marketing of the dimethyl propanephosphonate without labelling.

The examples below illustrate the inventive process without restricting it. The reaction mixtures were analysed by known gas chromatographic methods, and all percentages denote percentages by weight. There is reported herein two isomers of t dimethyl propanephosphonate, which are formed.

EXAMPLES

Example 1

A 2 l glass reactor with a flat flange ground joint equipped with a high-speed agitator, reflux condenser, thermometer, metering pump, vacuum pump, manometer, gas feed line connected via a nonreturn valve and needle valve having a propene gas cylinder situated on a balance is evacuated and charged with dry nitrogen. 500 g of dimethyl phosphite is introduced first under nitrogen and heated with gentle stirring and nitrogen blanketing to 90° C. After 90° C. is reached, the system is closed and a vacuum of 150 mbar is applied at maximum stirrer speed.

Propene is then introduced and addition of a solution of 105 g of dimethyl phosphite and 9.1 g of a 75% strength solution of tert-butyl peroxyneodecanoate in isododecane via metering pump is started, as a result of which the pressure increases from 150 mbar to 950 mbar. The propene addition is controlled in such a way that the pressure is maintained between 500 and 950 mbar. The reaction is exothermic and the internal temperature is controlled to 90° C. by regulating the heating. After 1.5 hours, 102.5 g of propene are metered in and the addition of propene and starter solution is stopped. The mixture is held at 90° C. for 1 hour. The batch is then brought to room temperature and the system purged with nitrogen.

Crude product weight 664.2 g, composition by gas chromatography: 43.84% dimethyl phosphite, 0.037% trimethyl phosphate, 54.86% dimethyl propanephosphonate, equivalent to 98.3% yield.

Example 2

Experimental procedure as in Example 1, but using a solution of 112.3 g of dimethyl phosphite and 4.8 g of a 75% strength solution of tert-butyl peroxyneodecanoate in isododecane as free-radical former.

Crude product weight 640.3 g, composition by gas chromatography: 42.78% dimethyl phosphite, 0.034% trimethyl phosphate, 56.09% dimethyl propanephosphonate, equivalent to 96.8% yield.

Example 3

Experimental procedure as in Example 1, but with an initial introduction of 605 g of dimethyl phosphite and using a solution of 88.4 g of 1,4-dioxane and 7.8 g of dilauroyl peroxide as free-radical former.

Crude product weight 785.7 g, composition by gas chromatography: 52.91% dimethyl phosphite, 0.032% trimethyl phosphate, 46.07% dimethyl propanephosphonate, equivalent to 97.6% yield.

Comparative Example 1

In a dimethyl propanephosphonate synthesis according to DE-A-2,043,520, Example 1, 0.6% by weight of trimethyl phosphate forms.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing dimethyl propanephosphonate, comprising reacting dimethyl phosphite with propene in the presence of a free-radical former at a reaction temperature of 60 to 95° C., the half life of the free-radical former being 0.1 to 20 min at the reaction temperature,
wherein the dimethyl propanephosphonate is prepared at a yield that is more than 95% and formation of trimethyl phosphate in the amount of more than 0.1% by weight is avoided.

2. Process according to claim 1, wherein the reaction temperature is 80 to 95° C.

3. Process according to claim 1, wherein the half life of the free-radical former is 0.5 to 10 min at the reaction temperature.

4. Process according to claim 1, wherein the free-radical former is used in an amount of 0.1 to 5 mol % based on propene.

5. Process according to claim 1, wherein the free-radical former is used in an amount of 0.3 to 2 mol %, based on propene.

6. Process according to claim 1, wherein tert-butyl peroxyneodecanoate or dilauroyl peroxide is used as free-radical former.

7. Process according to claim 1, wherein the molar ratio of dimethyl phosphite propene is 1.0:1.0 to 3.0:1.0.

8. Process according to claim 1, wherein the molar ratio of dimethyl phosphite to propene is 1.1:1.0 to 2.3:1.0.

9. Process according to claim 1, wherein dimethyl phosphite with a trimethyl phosphate content of 0 to 0.1% by weight is used.

10. Process according to claim 1, wherein dimethyl phosphite with a trimethyl phosphate content of 0 to 0.01% by weight is used.

11. Process according to claim 1, wherein the reaction is carried out at a pressure of 150 to 6 000 mbar (absolute).

12. Process according to claim 1, wherein the reaction is carried out at a pressure of 500 to 950 mbar (absolute).

* * * * *